(12) United States Patent
Shimizu

(10) Patent No.: US 6,274,218 B1
(45) Date of Patent: Aug. 14, 2001

(54) TOPSHEET FOR BODY FLUIDS ABSORBENT ARTICLE

(75) Inventor: Shingo Shimizu, Kagawa-ken (JP)

(73) Assignee: Uni-Charm, Ehime-ken (JP)

( * ) Notice: Subject to any disclaimer, the term of this patent is extended or adjusted under 35 U.S.C. 154(b) by 0 days.

(21) Appl. No.: 09/276,663

(22) Filed: Mar. 26, 1999

(30) Foreign Application Priority Data

Mar. 26, 1998 (JP) .................................................. 10-79966

(51) Int. Cl.$^7$ ...................................................... B32B 3/24
(52) U.S. Cl. .......................... 428/137; 428/131; 428/132; 428/913; 604/358; 604/378; 604/383; 604/385.01
(58) Field of Search .................... 428/131, 132, 428/137, 913; 604/358, 378, 383, 385.01

(56) References Cited

U.S. PATENT DOCUMENTS

| | | | | |
|---|---|---|---|---|
| 4,377,615 | * | 3/1983 | Suzuki et al. ........................ | 428/213 |
| 4,780,352 | * | 10/1988 | Palumbo ............................... | 428/138 |
| 4,806,411 | * | 2/1989 | McNingle, III et al. ............ | 428/139 |
| 5,264,268 | * | 11/1993 | Luceri et al. ........................ | 428/138 |
| 5,383,870 | * | 1/1995 | Takai et al. ......................... | 604/378 |
| 5,449,352 | * | 9/1995 | Nishino et al. ..................... | 604/383 |
| 5,522,811 | * | 6/1996 | Igaue et al. ......................... | 604/378 |
| 5,613,962 | * | 3/1997 | Kenmochi et al. .................. | 604/378 |
| 5,656,232 | * | 8/1997 | Takai et al. ......................... | 264/518 |
| 5,743,776 | * | 4/1998 | Igaue et al. ......................... | 442/414 |
| 5,873,963 | | 2/1999 | Trombetta et al. .................. | 156/622 |
| 5,885,267 | * | 3/1999 | Mishima et al. .................... | 604/378 |

FOREIGN PATENT DOCUMENTS

| | | |
|---|---|---|
| 0040447 | 11/1981 | (EP) . |
| 0749738 | 12/1996 | (EP) . |
| 64-20844 * | 1/1989 | (JP) . |
| 4-166151 * | 10/1990 | (JP) . |
| 4-35662 * | 2/1992 | (JP) . |
| 4-89054 * | 3/1992 | (JP) . |
| 4-152945 * | 5/1992 | (JP) . |

\* cited by examiner

Primary Examiner—William P. Watkins, III
(74) Attorney, Agent, or Firm—Lowe Hauptman Gilman & Berner, LLP

(57) ABSTRACT

A topsheet for body fluids absorbent article having a plurality of liquid-pervious apertures, the topsheet including an upper fibrous layer having a relatively low density and a lower fibrous layer having a relatively high density. Around each of the apertures, the first and second fibrous layers are integrated together so that the topsheet has a density progressively increasing from an upper surface towards a lower surface of the topsheet and has, in the proximity of the lower surface, a density further higher than in the second fibrous layer. The topsheet thus formed improves so that an upper surface thereof can be maintained in a dry state during use of the article having the topsheet.

8 Claims, 2 Drawing Sheets

TOPSHEET FOR BODY FLUIDS ABSORBENT ARTICLE

BACKGROUND OF THE INVENTION

The present invention relates to a topsheet for a body fluids absorbent article such as a disposable diaper, an incontinent pad, training pants, a sanitary napkin and the like.

Japanese Patent Application Disclosure Gazette (Kokai) No. Hei4-152945 discloses a topsheet for such purpose which is made of thermoplastic synthetic resin and a plurality of liquid-passages extending therethrough from its upper surface to its lower surface. Each of the liquid-passages has a higher density at its lower end than along its peripheral wall.

The known topsheet is based on a phenomenon that an amount of body fluids discharged on the topsheet rapidly transfer from a region of the topsheet having a relatively low fiber density toward a region of the topsheet having a relatively high fiber density. Specifically, through the liquid-passages of the topsheet, the body fluids transfers towards the lower ends of the respective liquid-passages having the relatively high density. These lower ends are usually kept in close contact with a liquid-absorbent core of the body fluids absorbent article and therefore the body fluids rapidly transfer from the lower ends into the absorbent core. The body fluids absorbent article using such a topsheet certainly allows the body fluids to be rapidly absorbed by the absorbent core without giving a wearer uncomfortable feeling of wetness. However, the wearer's body weight exerted on the liquid-absorbent core during use of the article causes the body fluids to flow back from the absorbent core toward the wearer's skin.

SUMMARY OF THE INVENTION

In view of the problem as has been described above, it is an object of the present invention to provide a topsheet improved so as to alleviate an uncomfortable feeling due to the back flow of the body fluids and at the same time to maintain the advantageous property achieved by the topsheet such that the body fluids can rapidly transfer to the liquid-absorbent core.

According to the present invention, there is provided a topsheet for body fluids absorbent article comprising: a sheet having an upper surface intended to be placed against a wearer's skin; a lower surface underlying the upper surface; a plurality of liquid-pervious apertures extending between the upper and lower surfaces; the topsheet having an upper part defined by a first fibrous layer and a lower part defined by a second fibrous layer having a density higher than that of the first fibrous layer; and around each of the apertures, the first and second fibrous layers being integrated together so that the topsheet has a density progressively increasing from the upper surface towards the lower surface and, at least in proximity of the lower surface, has a density further higher than in the second fibrous layer.

According to an embodiment of the present invention, a lower surface of the first fibrous layer and an upper surface of the second fibrous layer are intermittently bonded together by means of hot melt adhesive.

According to another embodiment of the present invention, the first fibrous layer and the second fibrous layer are hydrophilic and the second fibrous layer has a hydrophilicity higher than a hydrophilicity of the first fibrous layer.

According to still another embodiment of the present invention, the first fibrous layer is hydrophobic and the second fibrous layer is hydrophilic.

According to further another embodiment of the present invention, at least one of the first and second fibrous layers is formed by a nonwoven fabric.

According to yet another embodiment of the present invention, the first fibrous web has a basic weight of 10~30 g/m$^2$ and the second fibrous web has a basic weight of 10~100 g/m$^2$ and a density corresponding to at least 1.3 times of the first fibrous web.

The topsheet according to the present invention comprises the upper fibrous layer intended to be placed against a wearer's skin, the lower fibrous layer having a density higher than a density of the upper fibrous layer, and the apertures each having a density along its peripheral wall as well as in the proximity of thereof progressively increasing from the upper surface to the lower surface of the topsheet. Such feature advantageously facilitates the body fluids to transfer towards the absorbent core. Furthermore, it is difficult for the body fluids partially exuding from the absorbent core to transfer back towards the upper surface of the topsheet having a relatively low density. The upper surface of such topsheet can always remain dry and therefore can effectively alleviate an uncomfortable feeling of wetness from which a wearer of the conventional body fluids absorbent article has often suffered.

DETAILED DESCRIPTION OF THE PREFERRED EMBODIMENTS

Details of a topsheet for body fluids absorbent article according to the present invention will be more fully understood from the description given hereunder with reference to the accompanying drawings.

Figure 1:
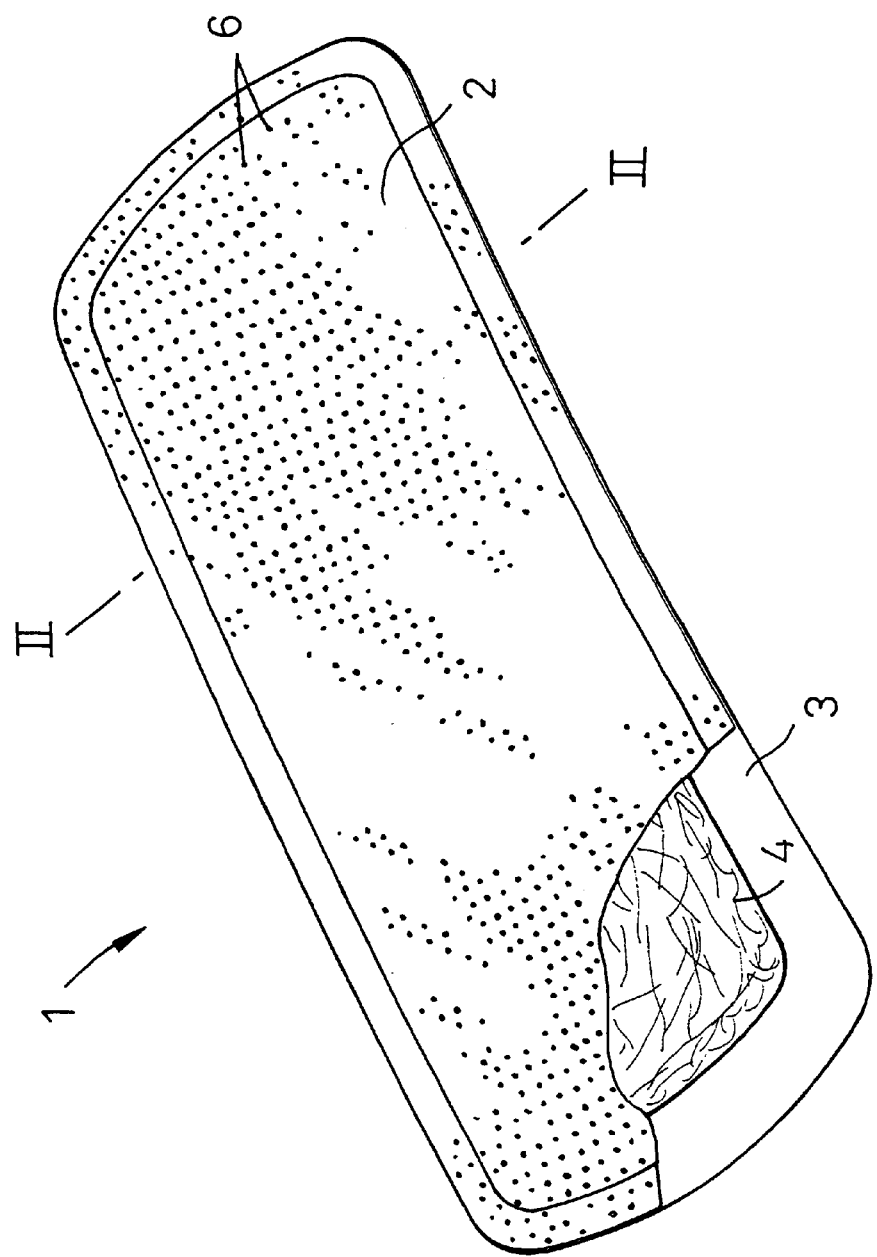
FIG. 1 is a perspective view showing a sanitary napkin as partially broken away.

FIG. 1 is a perspective view of a sanitary napkin 1 for menstruation as a specific example of a body fluids absorbent article adopting a topsheet according to the invention. The napkin 1 comprises a liquid-pervious topsheet 2 according to the invention, a liquid-impervious backsheet 3 and a liquid-absorbent core 4 disposed between these two sheets 2, 3. The topsheet 2 and the backsheet 3 extend outwards beyond peripheral edges of the absorbent core 4 so as to be placed upon each other and bonded together along these respective extensions.

The topsheet 2 is composed of a fibrous assembly formed with a plurality of apertures 6 each having a diameter of 0.2~5 mm, more preferably of 0.5~3 mm. So far as each of these apertures 6 can be regarded to have a substantially circular cross-section, a center-to-center distance of each pair of the adjacent apertures 6 is in a range of 0.5~20 mm, more preferably in a range of 0.7~10 mm. The backsheet 3 is made of a plastic sheet and the absorbent core 4 is made of a mixture of fluff pulp fiber and superabsorptive polymer articles.

Figure 2:
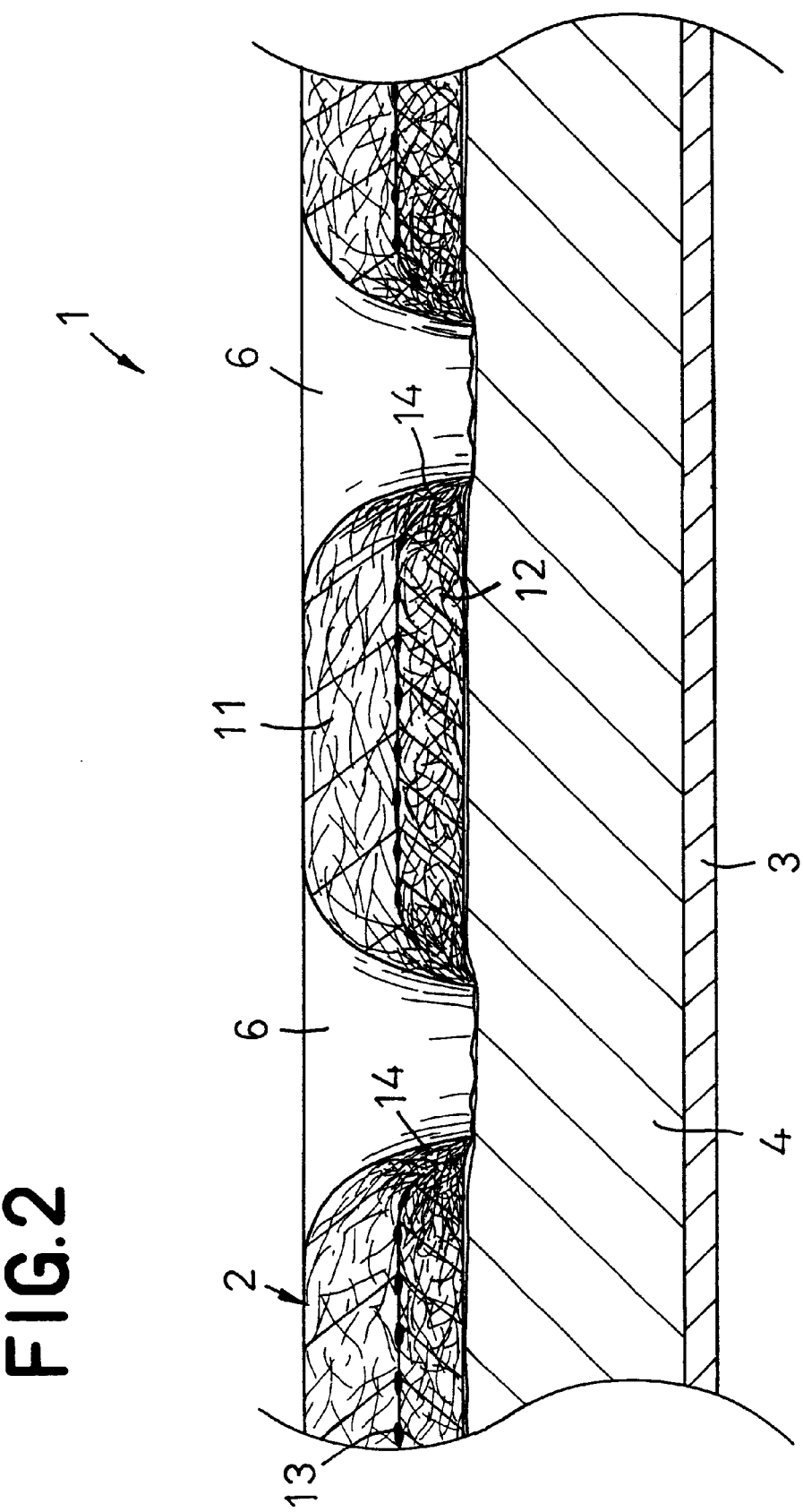
FIG. 2 is a sectional view showing important parts of the sanitary napkin shown in FIG. 1.

FIG. 2 is a sectional view showing important parts of the napkin 1. As shown, the topsheet 2 comprises a upper fibrous layer 11 intended to be placed against a wearer's skin and a lower fibrous layer 12 underlying the first fibrous layer 11 so as to be in contact with the absorbent core 4. The first fibrous layer 11 is formed by a web of thermoplastic fibers, preferably of crimped conjugated fibers mechanically entangled or heat-sealed together, or more preferably by a nonwoven fibrous sheet such as a nonwoven fabric, in any case, with a fineness of 1~6 deniers and with a basis weight of 10~30 g/m². The first fibrous layer 11 is hydrophobic and may be used either in the hydrophobic state or used after it has been treated to become hydrophilic. The second fibrous layer 12 is also formed by a plurality of thermoplastic synthetic fibers, each having a fineness of 1~10 deniers, mechanically entangled or heat-sealed together, more preferably provided in the form of a nonwoven fabric, in any case, with a basis weight of 10~100 g/m² and a density corresponding to at least 1.3 times of the density of the first fibrous layer 11. The second fibrous layer 12 is hydrophobic and may be used in the hydrophobic state, but, more preferably, used after it has been treated to have a hydrophilicity higher than the hydrophilicity of the first fibrous layer 11. While the first fibrous layer 11 and the second fibrous layer 12 are shown to be intermittently bonded together by means of hot melt adhesive 13, fibers in these fibrous layers 11, 12 may be bonded together, instead of utilizing the adhesive 13, by mechanically entangling them or by means of heat-sealing technique. Along a peripheral wall 14 of the aperture 6 and in the proximity of thereof, the density of the topsheet 2 progressively increases from its upper surface towards its lower surface and at least on the lower surface as well as in the proximity thereof, the topsheet 2 has a density higher than the density of the second fibrous layer 12.

The topsheet 2 constructed as has been described above advantageously enables rapid transfer of the body fluids from the first fibrous layer 11 in which both the hydrophilicity and the density are relatively low towards the second fibrous layer 12 in which both the hydrophilicity and the density are relatively high and thereby facilitates the upper surface of the topsheet 2 to be maintained in a dry state. The amount of body fluids having been absorbed by the second fibrous layer 12 is then partially absorbed by the absorbent core 4 underlying the second fibrous layer 12 and the rest laterally spreads within the second fibrous layer 12 before being absorbed by the absorbent core 4. In the proximity of the respective apertures 6, the body fluids transfer in the direction along which the density gradient increases, i.e., from the upper surface to the lower surface of the topsheet 2 and further toward the absorbent core 4. In this manner, the body fluids tend to transfer from the upper surface towards the lower surface of the topsheet 2 and further towards the absorbent core 4, preventing the body fluids from staying on the upper surface of the topsheet 2 for a long time and thereby ensuring that the upper surface of the topsheet 2 can rapidly restore to its dry state.

A wearer's body weight exerted on the absorbent core 4 which has already absorbed the body fluids may sometimes cause a partial amount of such body fluids to exude on the upper surface of the topsheet 2. However, one of the important features of the invention is that the density of the topsheet 2 progressively decreases from the second fibrous layer 12 to the first fibrous layer 11 and thereby can advantageously avoid such apprehension that the body fluids partially exuding from the absorbent core 4 might transfer back into the first fibrous layer 11 and eventually arrive at the wearer's skin. Accordingly, even after the absorbent core 4 has absorbed the body fluids, the upper surface of the topsheet 2 remains dry.

The topsheet 2 having its upper surface thus remaining dry does not give a wearer of the napkin any uncomfortable feeling of wetness.

What is claimed is:

1. A topsheet for a body fluids absorbent article comprising:

said topsheet having an upper surface intended to be placed against a wearer's skin;

a lower surface underlying said upper surface;

a plurality of liquid-pervious apertures extending between said upper and lower surfaces;

said topsheet having an upper part defined by a first fibrous layer and a lower part defined by a second fibrous layer having a density higher than that of said first fibrous layer, and around each of said apertures, said first and second fibrous layers being integrated together so that said topsheet has a density progressively increasing from said upper surface towards said lower surface and, at least in proximity of said lower surface, has a density further higher than the density in said second fibrous flayer.

2. The topsheet according to claim 1, wherein a lower surface of said first fibrous layer and an upper surface of said second fibrous layer are intermittently bonded together by means of hot melt adhesive.

3. The topsheet according to claim 1, wherein both said first fibrous layer and said second fibrous layer are hydrophilic and said second fibrous layer has a hydrophilicity higher than a hydrophilicity of said first fibrous layer.

4. The topsheet according to claim 1, wherein said first fibrous layer is hydrophobic and said second fibrous layer is hydrophilic.

5. The topsheet according to claim 1, wherein at least one of said first and second fibrous layers is formed by nonwoven fabric.

6. The topsheet according to claim 1, wherein said first fibrous web has a basic weight of 10~30 g/m² and said second fibrous web has basic weight of 10~100 g/m² and a density corresponding to at least 1.3 times of the density of the first fibrous web.

7. A topsheet for body fluids absorbent article comprising:

an upper surface intended to be placed against a wearer's skin;

a lower surface underlying said upper surface;

a plurality of liquid-pervious apertures extending between said upper and lower surfaces without protruding from the lower surface;

said topsheet having an upper part defined by a first fibrous layer and a lower part defined by a second fibrous layer having a density higher than that of said first fibrous layer wherein a lower surface of said first fibrous layer is entirely in close contact with an upper surface of said second fibrous layer, and around each of said apertures, said first and second fibrous layers being integrated together so that said topsheet has a density progressively increasing from said upper surface towards said lower surface and, at least in proximity of said lower surface, has a density further higher than in said second fibrous layer.

8. A topsheet for a body fluids absorbent article consisting essentially of:

said topsheet having an upper surface intended to be placed against a wearer's skin;

a lower surface underlying said upper surface;

a plurality of liquid-pervious apertures extending between said upper and lower surfaces;

said topsheet having an upper part defined by a first fibrous layer and a lower part defined by a second fibrous layer having a density higher than that of said first fibrous layer, and around each of said apertures, said first and second fibrous layers being integrated together so that said topsheet has a density progressively increasing from said upper surface towards said lower surface and, at least in proximity of said lower surface, has density further higher than the density in said second fibrous layer.

* * * * *